United States Patent

Suzuki et al.

[11] Patent Number: 5,407,936
[45] Date of Patent: Apr. 18, 1995

[54] BENZIMIDAZOLE DERIVATIVE, PROCESS FOR PREPARING THE SAME, ANTIEMETIC AGENT CONTAINING THE SAME AS ACTIVE INGREDIENT AND INTERMEDIATE COMPOUND FOR PREPARING THE SAME

[75] Inventors: Kenji Suzuki, Katsushika; Hiroshi Ohtaka, Osaka; Akio Ozaki, Osaka; Yasuo Morimoto, Osaka; Takayuki Sukamoto, Daito, all of Japan

[73] Assignee: Kanebo Ltd., Tokyo, Japan

[21] Appl. No.: 170,165

[22] PCT Filed: Jun. 22, 1992

[86] PCT No.: PCT/JP92/00794
§ 371 Date: Dec. 23, 1993
§ 102(e) Date: Dec. 23, 1993

[87] PCT Pub. No.: WO93/01176
PCT Pub. Date: Jan. 21, 1993

[30] Foreign Application Priority Data

Jul. 2, 1991 [JP] Japan .................. 3-189295
Dec. 25, 1991 [JP] Japan .................. 3-357558

[51] Int. Cl.$^6$ .................. A61K 31/495; C07D 403/04
[52] U.S. Cl. .................. 514/254; 544/370; 548/306.4; 548/310.4; 564/441; 564/442
[58] Field of Search .................. 544/370; 514/254

[56] References Cited

U.S. PATENT DOCUMENTS 4,093,726 6/1978 Winn et al. .................. 544/370

FOREIGN PATENT DOCUMENTS 512939 11/1992 European Pat. Off. .
126682 10/1975 Japan .
53-71088 6/1978 Japan .
1242574 9/1989 Japan .

OTHER PUBLICATIONS

Stevens et al, Chemical Abstracts, vol. 115, No. 49687 (1991).
*Advanced Organic Chemistry* by Jerry March (2nd ed.) pp. 1125–1126 (1977).

*Primary Examiner*—Emily Bernhardt
*Attorney, Agent, or Firm*—Foley & Lardner

[57] ABSTRACT

A benzimidazole derivative having the following formula (I):

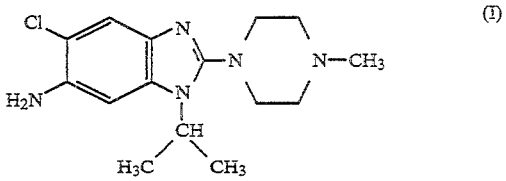

or a pharmaceutically acceptable acid addition salt thereof, a process for preparing the same, an antiemetic agent containing the same as an active ingredient and an intermediate compound for preparing the same. The above novel benzimidazole derivative has a continuous 5-HT$_3$ antagonistic activity, shows preventive and therapeutic effects against vomiting caused by cisplatin and has a low toxicity, and hence, is useful as an antiemetic agent against vomiting due to chemotherapeutic treatment with cisplatin etc.

3 Claims, No Drawings

BENZIMIDAZOLE DERIVATIVE, PROCESS FOR PREPARING THE SAME, ANTIEMETIC AGENT CONTAINING THE SAME AS ACTIVE INGREDIENT AND INTERMEDIATE COMPOUND FOR PREPARING THE SAME

TECHNICAL FIELD

The present invention relates to a novel benzimidazole derivative, a process for preparing the same, an antiemetic agent containing the same as an active ingredient and an intermediate compound for preparing the same.

BACKGROUND ART

Chemotherapeutics such as cisplatin are indispensable to the treatment of cancer. However, the chemotherapeutics cause side effects such as vomiting and hence make it difficult to continue the treatment.

Recently, it has become known that the occurrence of vomiting is associated with one of receptors of serotonin [5-hydroxytryptamine, hereinafter referred to as "5-HT"]. 5-HT is one of neurotransmitters in the living body and receptors of 5-HT have been classified into three groups, $5\text{-HT}_1$, $5\text{-HT}_2$ and $5\text{-HT}_3$. Among them, $5\text{-HT}_3$ receptor is associated with vomiting due to chemotherapeutic treatment of cancer. That is, 5-HT is released by administration of the chemotherapeutics and the released 5-HT is bound to the abdominal $5\text{-HT}_3$ receptor, and thereby the chemical receptor trigger in the bulb fourth ventricle is stimulated via the abdominal vagus nerve, and then the vomiting center is stimulated to induce vomiting.

It has been reported that Ondansetron (GR38032F, see the following formula) having $5\text{-HT}_3$ antagonistic activity is effective for inhibition of vomiting caused by the administration of the chemotherapeutics such as cisplatin [Cancer. Chemother. Pharmacol., 23, 389–391 (1989)].

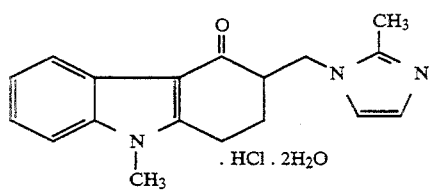

On the other hand, there has already been known the use of 2-(4-methyl-1-piperazinyl)benzimidazole derivatives as a drug. For example, Japanese Patent First Publication No. 50-126682 discloses 2-(4-methyl-1-piperazinyl)benzimidazole derivatives having analgesic and antiinflammatory activities, and 1-methyl-2-(4-methyl-1-piperazinyl)benzimidazole (Compound A) etc are exemplified. However, the $5\text{-HT}_3$ antagonistic activity and the resulting antiemetic activity of 2-(4-methyl-1-piperazinyl)benzimidazole derivatives have not yet been known (see Experiment 1 disclosed hereinafter).

The present inventors have conducted a variety of studies for developing a novel antiemetic agent having a strong and long-lasting inhibitory activity against vomiting due to chemotherapeutic treatment of cancer with cisplatin etc. based on the $5\text{-HT}_3$ antagonistic activity.

DISCLOSURE OF THE INVENTION

The present inventors have extensively studied, and as a result, have found that a novel benzimidazole derivative of the following formula (I) or a pharmaceutically acceptable acid addition salt thereof can satisfy the above requirement and so the present invention has been completed.

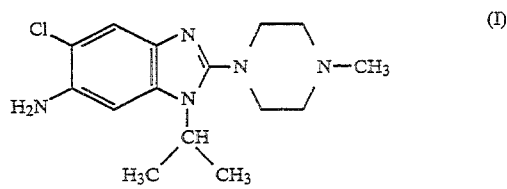

BEST MODE FOR PRACTICING THE INVENTION

The benzimidazole derivative (I) of the present invention can be prepared by treating the compound of the following formula (II):

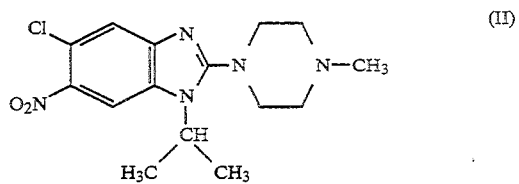

with usually 4 to 7 equivalents of a reducing agent in an inert solvent at a temperature between room temperature to reflux conditions for 1 to 10 hours. The reducing agent includes, for example, a combination of zinc and hydrochloric acid; iron and hydrochloric acid; stannous chloride and hydrochloric acid; and the like.

The compound (I) of the present invention can optionally be converted into a pharmaceutically acceptable acid addition salt thereof by the conventional procedure.

The pharmaceutically acceptable acid addition salt of the compound of the present invention includes a salt with an inorganic acid such as hydrochloric acid, sulfuric acid, etc, or a salt with an organic acid such as maleic acid, fumaric acid, etc.

The compound (II) (intermediate compound) used in the above process for preparation is a novel compound which has hitherto never been described in any literature and can be prepared, for example, by the following process (a) or (b).

Process (a):

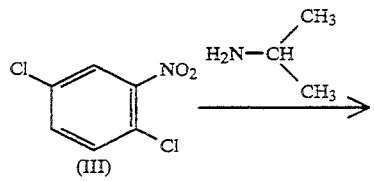

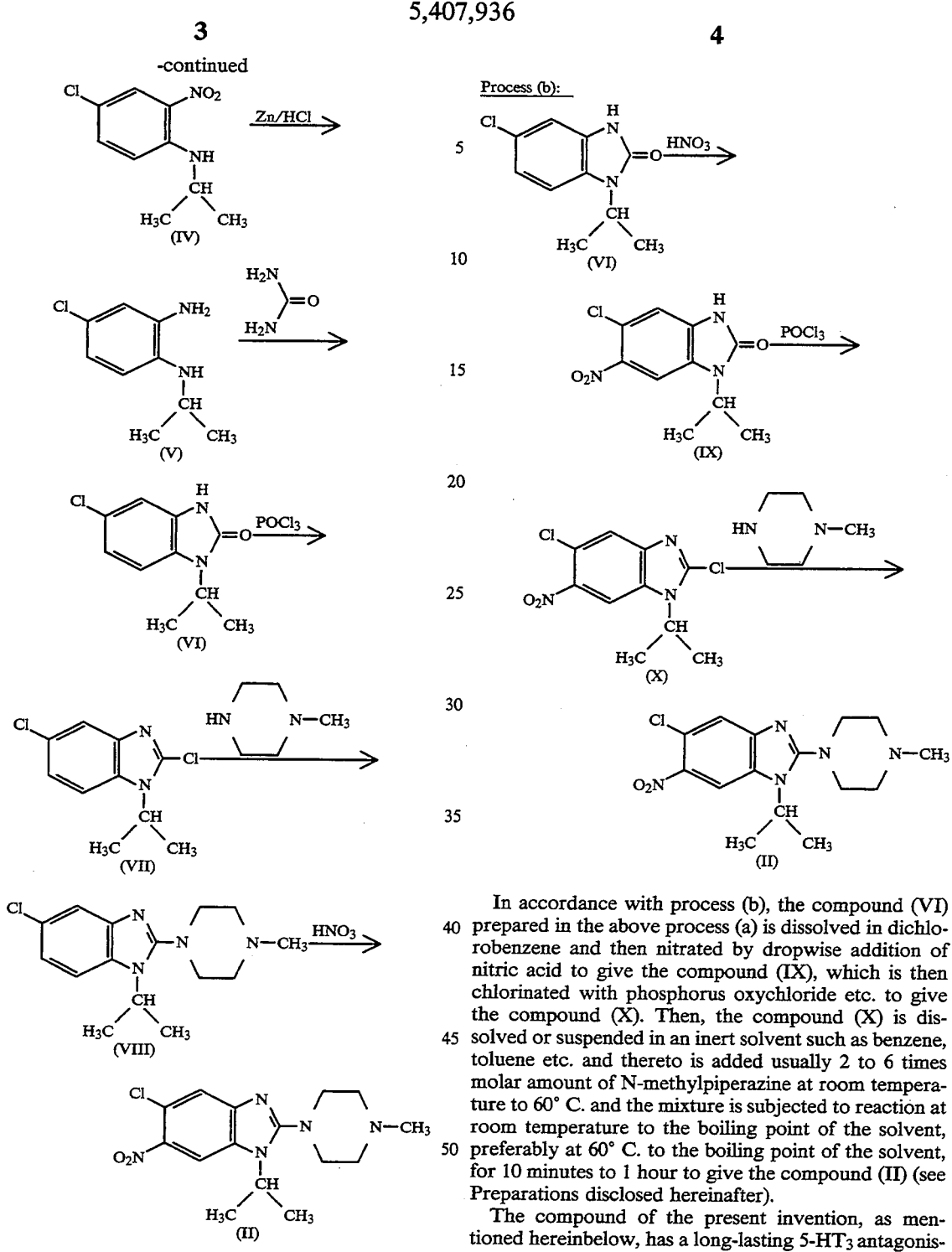

In accordance with the process (a), the compound (III) is reacted with isopropylamine to give the compound (IV). Then, the compound (IV) is reacted with zinc in the presence of hydrochloric acid to give the compound (V), which is then reacted with urea to give the compound (VI). The compound (VI) is reacted with phosphorus oxychloride to give the compound (VII), which is then reacted with N-methylpiperazine to give the compound (VIII). Then, the compound (VIII) is reacted with fuming nitric acid in acetic acid or reacted with concentrated nitric acid in concentrated sulfuric acid at a lower temperature to give the compound (II) (see Preparations disclosed hereinafter).

In accordance with process (b), the compound (VI) prepared in the above process (a) is dissolved in dichlorobenzene and then nitrated by dropwise addition of nitric acid to give the compound (IX), which is then chlorinated with phosphorus oxychloride etc. to give the compound (X). Then, the compound (X) is dissolved or suspended in an inert solvent such as benzene, toluene etc. and thereto is added usually 2 to 6 times molar amount of N-methylpiperazine at room temperature to 60° C. and the mixture is subjected to reaction at room temperature to the boiling point of the solvent, preferably at 60° C. to the boiling point of the solvent, for 10 minutes to 1 hour to give the compound (II) (see Preparations disclosed hereinafter).

The compound of the present invention, as mentioned hereinbelow, has a long-lasting 5-$HT_3$ antagonistic activity and shows preventive and therapeutic effects against vomiting induced by cisplatin and has a low toxicity, and hence, can suitably be used as an antiemetic agent against vomiting due to the chemotherapeutic treatment of cancer with cisplatin etc.

When the compound of the present invention is used for treatment of vomiting due to chemotherapeutic treatment of cancer, it is formulated into the conventional dosage form and then used as oral preparations or injections.

The oral dosage form includes solid preparations such as tablets, granules, powders, capsules, etc. as well as liquid preparations such as syrups etc. These dosage forms can be prepared by the conventional procedure.

The solid preparations can be formulated using the conventional pharmaceutical additives, for example, lactose, corn starch, crystalline cellulose, hydroxypropylcellulose, magnesium stearate, light anhydrous silicic acid, talc, etc. The capsules can be prepared by filling suitable capsules with the thus prepared granules, powders, etc. The syrups can be prepared by dissolving or suspending the compound of the present invention in an aqueous solution containing sucrose, carboxymethylcellulose, etc. The injections can be prepared by the conventional procedure and may optionally be supplemented with a stabilizing agent, a solubilizing agent, etc.

The dose of the compound of the present invention may vary depending on the severity of the symptom, the body weight, the age of the patient, etc. but, in case of the oral administration, is usually 0.2 to 200 μg/kg per day in adults, which is administered in a single dose or in multiple doses divided into 2 or 3 doses. In case of the injections, the dose is usually 0.1 to 100 μg/kg per day in adults, which is administered in a single dose or in multiple doses divided into 2 to 3 doses.

EFFECTS OF THE INVENTION

The compound of the present invention exhibits strong antagonistic activity against Bezold-Jarisch reflex induced by 5-HT (5-HT$_3$ antagonistic activity) and this activity continues for a long period of time (see Experiment 1 disclosed hereinafter). The compound of the present invention also shows strong preventive and therapeutic effects against vomiting caused by cisplatin (see Experiment 2 disclosed hereinafter). In addition, the compound of the present invention has a low toxicity (see Experiment 3 disclosed hereinafter). Therefore, the compound of the present invention is useful as an antiemetic agent having strong, long-lasting inhibitory activity against vomiting due to chemotherapeutic treatment of cancer with cisplatin etc. with high safety.

The effects of the compound of the present invention are illustrated by the following Experiments.

EXPERIMENT 1

5-HT$_3$ antagonistic activity:
(Test compounds)

(1) 6-Amino-5-chloro-1-isopropyl-2-(4-methyl-1-piperazinyl)benzimidazole (Compound 1 of the present invention)
(2) 6-Amino-5-chloro-1-isopropyl-2-(4-methyl-1-piperazinyl)benzimidazole dimaleate (Compound 2 of the present invention)
(3) 1-Methyl-2-(4-methyl-1-piperazinyl)benzimidazole (Compound A, the compound described in Japanese Patent First Publication No. 50-126682)
(4) Ondansetron (Reference compound)
(Experimental procedure)

The 5-HT$_3$ antagonistic activity was measured in accordance with the method by Collins et al. [Br. J. Pharmacol., 80, 570P (1983)] using as an index the inhibitory activity against reflective bradycardia [Bezold-Jarisch reflex] induced by 5-HT.

That is, S.D. male rats (weighing 200 to 350 g) were anesthetized by intraperitoneal administration of urethane (1.25 mg/kg) and introduced with cannula into the carotid and the pulse frequency was measured. 5-HT was dissolved in physiological saline and intravenously administered (0.04 mg/kg). The test compounds were dissolved in physiological saline or physiological saline containing 5% ethanol and intravenously administered five minutes before the administration of 5-HT.

ED$_{50}$ values were obtained from a dose-response curve of inhibitory rate of reflective bradycardia by the test compounds and the 5-HT$_3$ antagonistic activity was compared.

In addition, the test compounds (about 25 times amount of the above ED$_{50}$ value) and 5-HT were intravenously administered in the same manner as mentioned above and thereafter 5-HT (0.04 mg/kg) was intravenously administered with the passage of time. The time until the inhibitory rate of reflective bradycardia by the test compounds became 20% or less was determined and the duration of the 5-HT$_3$ antagonistic activity was obtained (as to Compound A, the measurement was not done since said antagonistic activity was quite low as compared to the compound of the present invention).

(Test results)
The results are shown in Table 1.

TABLE 1

(Antagonistic activity against Bezold-Jarisch reflex)

| Test compounds | ED$_{50}$ (μg/kg, i.v.) [95% Confidence limits] | Dose (μg/kg, i.v.) | Duration time (hr) |
|---|---|---|---|
| Compound 1 of the invention | 0.044[0.013–0.068] | 1.0 | >>8 |
| Compound 2 of the invention | 0.071[0.050–0.097] | 1.0 | >>8 |
| Compound A | >3.0 | — | — |
| Reference compound | 4.0[2.7–6.3] | 100 | 2 |

EXPERIMENT 2

Preventive and therapeutic effects against vomiting induced by cisplatin:
(Test compounds)

(1) 6-Amino-5-chloro-1-isopropyl-2-(4-methyl-1-piperazinyl)benzimidazole (Compound 1 of the present invention)
(2) 6-Amino-5-chloro-1-isopropyl-2-(4-methyl-1-piperazinyl)benzimidazole dimaleate (Compound 2 of the present invention)
(3) Ondansetron (Reference compound)
(Experimental procedure)

The experiment was conducted in accordance with the method by Costall et al. [Neuropharmacology, 26, 1321–1326 (1987)].

That is, male ferrets (weighing 1.0 to 1.6 kg, three animals in each group) underwent an implant operation of cannula at the jugular vein for intravenous administration. For evaluating the preventive effects, the test compounds dissolved in a physiological saline or in a physiological saline containing 5% ethanol or a physiological saline (control) were intravenously administered to the ferrets three days after the operation, then after 5 minutes, cisplatin (10 mg/kg) dissolved in a physiological saline was intravenously administered to the ferrets over 30 seconds, and a number of vomiting caused between just after the administration of cisplatin and 4 hours after the administration was measured. As to the therapeutic effects, cisplatin (10 mg/kg) dissolved in a physiological saline was intravenously administered to the ferrets three days after the operation over 30 seconds. After appearance of vomiting (about 80 minutes after the administration of cisplatin), the test compounds dissolved in a physiological saline or in a physiological saline containing 5% ethanol or a physiological saline (control) were intravenously administered to the ferrets and then a number of vomiting occurred during 4 hours thereafter was counted. The inhibitory rate was calculated by the following formula: Inhibitory rate (%)={1−(mean number of vomiting in the group administered with the test compound/mean number of vomiting in the control group)}×100

(Test results)

The results are shown in Table 2.

TABLE 2

(Preventive and therapeutic effects against cisplatin-induced vomiting)

| Test compounds | Dose (mg/kg, i.v.) | Inhibitory rate (%) Preventive effect | Inhibitory rate (%) Therapeutic effect |
|---|---|---|---|
| Compound 1 of the invention | 0.01 | 100 | 100 |
| Compound 2 of the invention | 0.01 | 85 | 100 |
| Reference compound | 0.1 | 31 | 77 |

EXPERIMENT 3

Acute toxicity:

(Test compounds)

The same as in Experiment 2

(Experimental procedure)

ddY Male mice (weighing 20 to 30 g, five animals in each group) were fasted for a night and the test compounds (100 mg/kg) dissolved in a physiological saline or in a physiological saline containing an equimolar amount of hydrochloric acid were intravenously administered to the mice and death of the animals were observed for 7 days after the administration.

(Test results)

Death was not observed in the group administered with the compounds of the present invention whereas all animals were dead in the group administered with the reference compound. Therefore, the compound of the present invention has a lower toxicity as compared to the reference compound (Ondansetron).

EXAMPLE

The present invention is illustrated in more detail by the following Preparations and Examples.

Preparation 1

4-Chloro-N-isopropyl-2-nitroaniline (the compound of the formula (IV)):

2,5-Dichloronitrobenzene (150 g) was added to isopropylamine (150 g) and the mixture was stirred in a sealed tube at 100° C. for 4 hours. After cooling, water was added to the reaction mixture and the mixture was extracted with ethyl acetate. The ethyl acetate layer was washed with water and dried over anhydrous magnesium sulfate and then the solvent was distilled off under reduced pressure to give 4-chloro-N-isopropyl-2-nitroaniline (163 g). A part of the obtained product was recrystallized from methanol, which showed the following physical properties:

mp 72.0°–74.0° C. NMR (CDCl$_3$, δ ppm): 1.33 (6H, d), 3.56–4.20 (1H, m), 6.89 (1H, d), 7.44 (1H, dd), 8.09 (1H, brs), 8.21 (1H, d) Elemental analysis (for C$_9$H$_{11}$ClN$_2$O$_2$) Calculated (%): C,50.36; H,5.17; N,13.05 Found (%): C,50.21; H,5.10; N,13.05

Preparation 2

2-Amino-4-chloro-N-isopropylaniline (the compound of the formula (V)):

4-Chloro-N-isopropyl-2-nitroaniline (8 g) was dissolved in ethanol (20 ml) and thereto zinc powder (9.8 g) was added, and concentrated hydrochloric acid (20 ml) was added in portions. The mixture was neutralized with aqueous ammonia and extracted with ethyl acetate. The ethyl acetate layer was washed with water and dried over anhydrous magnesium sulfate and the solvent was distilled off under reduced pressure. The residue was distilled (bp 90° C./0.4 mmHg) to give 2-amino-4-chloro-N-isopropylaniline (4.2 g).

mp 35.0°–36.0° C. NMR (CDCl$_3$, δ ppm): 1.22 (6H, d), 2.50–4.10 (4H, m), 6.38–7.08 (3H, m) Elemental analysis (for C$_9$H$_{13}$ClN$_2$) Calculated (%): C,58.54; H,7.10; N,15.17 Found (%): C,58.39; H,7.09; N,15.33

Preparation 3

5-Chloro-1-isopropylbenzimidazol-2-one (the compound of the formula (VI)):

A mixture of 2-amino-4-chloro-N-isopropylaniline (14 g) and urea (15 g) was stirred at 160° C. for 3.5 hours. After cooling, water was added to the reaction mixture and the mixture was extracted with ethyl acetate. The ethyl acetate layer was washed with diluted hydrochloric acid, an aqueous sodium hydroxide solution, a saturated sodium chloride solution and dried over anhydrous magnesium sulfate and then the solvent was distilled off under reduced pressure. To the residue was added isopropyl alcohol and the obtained crystal was separated by filtration and recrystallized from acetonitrile to give 5-chloro-1-isopropylbenzimidazol-2-one (7 g).

mp 183.0°–186.0° C. NMR (CDCl$_3$, δ ppm): 1.55 (6H, d), 4.46–5.01 (1H, m), 6.85–7.41 (3H, m) Elemental analysis (for C$_{10}$H$_{11}$ClN$_2$O) Calculated (%): C,57.02; H,5.26; N,13.30 Found (%): C,57.07; H,5.32; N,13.38

Preparation 4

2,5-Dichloro-1-isopropylbenzimidazole (the compound of the formula (VII)):

5-Chloro-1-isopropylbenzimidazol-2-one (81 g) in phosphorus oxychloride (207 g) was refluxed for 1 hour. The mixture was left to stand for cooling and then the reaction mixture was poured into ice-water and extracted with ethyl acetate. The ethyl acetate layer was washed with an aqueous sodium hydroxide solution, water and dried over anhydrous magnesium sulfate and then the solvent was distilled off under reduced pressure. To the residue was added acetonitrile (400 ml) and the insoluble material was removed by filtration and the solvent was distilled off under reduced pressure to give 2,5-dichloro-1-isopropylbenzimidazole (73 g). A part of the obtained product was subjected to silica gel column chromatography [eluted with chloroform] and recrystallized from hexane, which showed the following physical properties:

mp 72.0°–75.0° C. NMR (CDCl$_3$, δ ppm): 1.61 (6H, d), 4.32–5.29 (1H, m), 7.12 (1H, dd), 7.37 (1H, d), 7.58 (1H, d) Elemental analysis (for C$_{10}$H$_{10}$Cl$_2$N$_2$) Calculated (%): C,52.42; H,4.40; N,12.23 Found (%): C,52.56; H,4.49; N,12.37

Preparation 5

5-Chloro-1-isopropyl-2-(4-methyl-1-piperazinyl)benzimidazole (the compound of the formula (VIII)):

A mixture of 2,5-dichloro-1-isopropylbenzimidazole (7 g) and N-methylpiperazine (10 g) was stirred at 140° C. for 3.5 hours. After cooling, 2N hydrochloric acid was added to the mixture and the mixture was washed with ethyl acetate. The 2N hydrochloric acid layer was made basic with an aqueous 2N sodiumhydroxide solution and extracted with ethyl acetate. The ethyl acetate layer was washed with a saturated sodium chloride solution and dried over anhydrous magnesium sulfate and then the solvent was distilled off under reduced pressure to give 5-chloro-1-isopropyl-2-(4-methyl-1-piperazinyl)benzimidazole (4.2 g). A part of the obtained product was recrystallized from acetonitrile, which showed the following physical properties:

mp 124.0°–125.5° C.

NMR (CDCl$_3$, δ ppm): 1.59 (6H, d), 2.39 (3H, s), 2.50–2.86 (4H, m), 3.15–3.60 (4H, m), 4.34–4.98 (1H, m), 7.13 (1H, dd), 7.39 (1H, d), 7.67 (1H, d) Elemental analysis (for C$_{15}$H$_{21}$ClN$_4$) Calculated (%): C,61.53; H,7.23; N,19.13 Found (%): C,61.30; H,7.40; N,19.25

Preparation 6

5-Chloro-1-isopropyl-6-nitrobenzimidazol-2-one (the compound of the formula (IX)):

5-Chloro-1-isopropylbenzimidazol-2-one (4.0 g) was dissolved in o-dichlorobenzene (80 ml) and thereto was added dropwise 70% nitric acid (2.0 g). The mixture was stirred at 60° C. for 1 hour and left to stand for cooling. The precipitated crystal was separated by filtration and washed with diethyl ether and water to give 5-chloro-1-isopropyl-6-nitrobenzimidazol-2-one (4.1 g). A part of the obtained product was recrystallized from ethanol, which showed the following physical properties:

mp 270.0°–272.0° C. NMR (DMSO-d$_6$, δ ppm): 1.46 (6H, d), 4.25–4.95 (1H, m), 7.25 (1H, s), 8.03 (1H, s) Elemental analysis (for C$_{10}$H$_{10}$ClN$_3$O$_3$) Calculated (%): C,46.98; H,3.94; N,16.44 Found (%): C,47.04; H,3.86; N,16.59

Preparation 7

2,5-Dichloro-1-isopropyl-6-nitrobenzimidazole (compound of the formula (X)):

To 5-chloro-1-isopropyl-6-nitrobenzimidazol-2-one (1.0 g) were added ethylene carbonate (0.7 g) and phosphorus oxychloride (1.1 ml) and the mixture was refluxed for 5 hours. Phosphorus oxychloride was distilled off under reduced pressure and the residue was dissolved in ethyl acetate and the solution was added to ice-water and the mixture was neutralized with an aqueous sodium hydroxide solution. The organic layer was washed with water and dried over anhydrous magnesium sulfate and then the solvent was distilled off under reduced pressure to give 2,5-dichloro-1-isopropyl-6-nitrobenzimidazole (0.9 g). A part of the obtained product was recrystallized from ethanol, which showed the following physical properties:

mp 150.5°–152.5° C. NMR (CDCl$_3$, δ ppm): 1.66 (6H, d), 4.55–5.30 (1H, m), 7.79 (1H, s), 8.11 (1H, s) Elemental analysis (for C$_{10}$H$_9$Cl$_2$N$_3$O$_2$)

Calculated (%): C,43.82; H,3.31; N,15.33
Found (%): C,44.97; H,3.38; N,15.39

Preparation 8

5-Chloro-1-isopropyl-2-(4-methyl-1-piperazinyl)-6-nitrobenzimidazole (the compound of the formula (II)):

5-Chloro-1-isopropyl-2-(4-methyl-1-piperazinyl)benzimidazole (2.7 g) was dissolved in acetic acid (15 ml). To the solution was added fuming nitric acid (3 ml) at 0° C. and then the mixture was stirred at 60° C. for 1 hour. The reaction mixture was poured into water and the mixture was made basic with an aqueous sodium hydroxide solution and extracted with chloroform. The chloroform layer was washed with water and dried over anhydrous magnesium sulfate and then the solvent was distilled off under reduced pressure. The residue was subjected to silica gel column chromatography [eluted with chloroform-methanol (10:1, v/v)] to give 5-chloro-1-isopropyl-2-(4-methyl-1-piperazinyl)-6-nitrobenzimidazole (1.8 g). A part of the obtained product was recrystallized from acetonitrile, which showed the following physical properties:

mp 160.0°–161.5° C. NMR (CDCl$_3$, δ ppm): 1.62 (6H, d), 2.40 (3H, s), 2.48–2.90 (4H, m), 3.16–3.70 (4H, m), 4.32–5.00 (1H, m), 7.72 (1H, s), 8.12 (1H, s) Elemental analysis (for C$_{15}$H$_{20}$ClN$_5$O$_2$) Calculated (%): C,53.33; H,5.97; N,20.73 Found (%): C,53.21; H,5.85; N,20.73

Preparation 9

5-Chloro-1-isopropyl-2-(4-methyl-1-piperazinyl)-6-nitrobenzimidazole (the compound of the formula (II)):

5-Chloro-1-isopropyl-2-(4-methyl-1-piperazinyl)benzimidazole (24.1 g) was dissolved in concentrated sulfuric acid (160 ml). To the solution were added dropwise concentrated nitric acid (7.8 g) and concentrated sulfuric acid (20.2 g) at 0° C. and the mixture was stirred at 0° C. for 5 minutes. The reaction mixture was poured into water and the mixture was made basic with an aqueous sodium hydroxide solution and extracted with chloroform. The chloroform layer was washed with water and dried over anhydrous magnesium sulfate and then the solvent was distilled off under reduced pressure to give 5-chloro-1-isopropyl-2-(4-methyl-1-piperazinyl)-6-nitrobenzimidazole (25.5 g). A part of the obtained product was recrystallized from acetonitrile, which showed the physical properties consistent with those in Preparation 8.

Preparation 10

5-Chloro-1-isopropyl-2-(4-methyl-1-piperazinyl)-6-nitrobenzimidazole (the compound of the formula (II)):

2,5-Dichloro-1-isopropyl-6-nitrobenzimidazole (4.6 g) was suspended in toluene (31 ml) and to the suspension was added dropwise N-methylpiperazine (8.4 g) and then the mixture was refluxed for 30 minutes. To the reaction solution was added ethyl acetate and the mixture was washed with water and then extracted with 2N hydrochloric acid. The water layer was separated and made basic with an aqueous sodium hydroxide solution and then extracted with ethyl acetate. The organic layer was washed with water and dried over anhydrous magnesium sulfate and then the solvent was distilled off under reduced pressure to give 5-chloro-1-isopropyl-2-(4-methyl-1-piperazinyl)-6-nitrobenzimidazole (4.8 g). A part of the obtained product was recrystallized from acetonitrile, which showed the physical properties consistent with those in Preparation 8.

EXAMPLE 1

6-Amino-5-chloro-1-isopropyl-2-(4-methyl-1-piperazinyl)benzimidazole (compound of the formula (I)):

5-Chloro-1-isopropyl-2-(4-methyl-1-piperazinyl)-6-nitrobenzimidazole (1.2 g) was dissolved in 2.5N hydrochloric acid (20 ml) and thereto was added zinc powder (1.5 g) in portions and the mixture was stirred at 80° C. for 4 hours. The reaction mixture was made basic with an aqueous ammonia and extracted with chloroform. The chloroform layer was washed with water and dried over anhydrous magnesium sulfate and then the solvent was distilled off under reduced pressure. The residue was recrystallized from acetonitrile to give 6-amino-5-chloro-1-isopropyl-2-(4-methyl-1-piperazinyl)benzimidazole (0.6 g) as colorless crystal.

mp 192.0°–193.0° C. NMR (CDCl$_3$, δ ppm): 1.53 (6H, d), 2.38 (3H, s), 2.48–2.80 (4H, m), 3.05–3.47 (4H, m), 4.03 (2H, brs), 4.30–4.92 (1H, m), 6.84 (1H, s), 7.57 (1H, s) Elemental analysis (for $C_{15}H_{22}ClN_5$) Calculated (%): C,58.53; H,7.20; N,22.75 Found (%): C,58.48; H,7.06; N,22.77

Dihydrochloride

6-Amino-5-chloro-1-isopropyl-2-(4-methyl-1-piperazinyl)benzimidazole (2.0 g) was dissolved in ethanol (5 ml) and thereto was added 11% (w/w) hydrochloric acid-ethanol (10 ml). After cooling, the precipitated crystal was separated by filtration and the obtained crystal was recrystallized from a mixed solvent of ethanol-methanol to give 6-amino-5-chloro-1-isopropyl-2-(4-methyl-1-piperazinyl)benzimidazole dihydrochloride (1.7 g) as colorless crystal.

mp 275.0°–280.0° C. (dec.) NMR (CD$_3$OD, δ ppm): 1.69 (6H, d), 3.02 (3H, s), 3.43–4.09 (8H, m), 4.30–5.30 (5H, m), 7.41 (1H, s), 7.55 (1H, s) Elemental analysis (for $C_{15}H_{22}ClN_5 \cdot 2HCl$) Calculated (%): C,47.31; H,6.35; N,18.39 Found (%): C,46.96; H,6.19; N,18.29

Dimaleate

Methanol (5 ml) was added to maleic acid (0.8 g) and the mixture was heated to dissolve. To the solution was added 6-amino-5-chloro-1-isopropyl-2-(4-methyl-1-piperazinyl)benzimidazole (1.0 g) dissolved in methanol (5 ml). After cooling, the precipitated crystal was separated by filtration off and the obtained crystal was recrystallized from acetonitrile to give 6-amino-5-chloro-1-isopropyl-2-(4-methyl-1piperazinyl)benzimidazole dimaleate (1.2 g) as colorless crystal.

mp 171.0°–172.0° C. (dec.) NMR (DMSO-d$_6$, δ ppm): 1.51 (6H, d), 2.93 (3H, s), 3.16–3.71 (8H, m), 4.32–5.00 (1H, m), 6.17 (4H, s), 7.08 (1H, s), 7.34 (1H, s), 10.00 (6H, brs) Elemental analysis (for $C_{15}H_{22}ClN_5 \cdot 2C_4H_4O_4$) Calculated (%): C,51.16; H,5.60; N,12.97

Found (%): C,50.97; H,5.42; N,13.06

EXAMPLE 2

Preparation of injections

6-Amino-5-chloro-1-isopropyl-2-(4-methyl-1-piperazinyl)benzimidazole dimaleate (2 g) is dissolved in purified water for injections to make a total volume of 1000 ml. Then, the solution is subjected to sterile filtration with a membrane filter (0.2 μm) and each 1 ml of the solution is poured into ampules and the ampules are sealed, which are then sterilized at 120° C. for 20 minutes.

EXAMPLE 3

Preparation of tablets:

| (Formulation) Component | Amount (g) |
| --- | --- |
| 6-Amino-5-chloro-1-isopropyl-2-(4-methyl-1-piperazinyl)benzimidazole | 2 |

-continued

Preparation of tablets:

| (Formulation) Component | Amount (g) |
| --- | --- |
| Lactose | 80.5 |
| Corn starch | 28 |
| Crystalline cellulose | 25 |
| Hydroxypropylcellulose | 3.5 |
| Magnesium stearate | 1 |
| Total | 140 |

(Procedure)

The above components are mixed together homogeneously and the mixture is tableted by the conventional procedure to give tablets (each 140 mg).

EXAMPLE 4

Preparation of powders

| (Formulation) Component | Amount (g) |
| --- | --- |
| 6-Amino-5-chloro-1-isopropyl-2-(4-methyl-1-piperazinyl)benzimidazole | 20 |
| Lactose | 825 |
| Corn starch | 150 |
| Light anhydrous silicic acid | 5 |
| Total | 1000 |

(Procedure)

The above components are thoroughly mixed together to give a homogeneous mixed powder and each 1 g of the powder is separately wrapped.

We claim:

1. A benzimidazole derivative having the following formula:

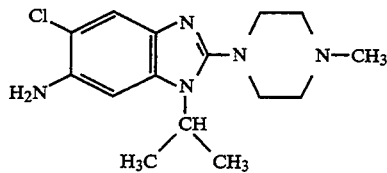

or a pharmaceutically acceptable acid addition salt thereof.

2. An antiemetic composition comprising a benzimidazole derivative having the following formula:

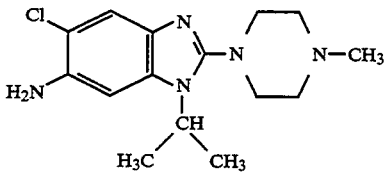

or a pharmaceutically acceptable acid addition salt thereof, and a pharmaceutically acceptable carrier.

3. A compound having the following formula:

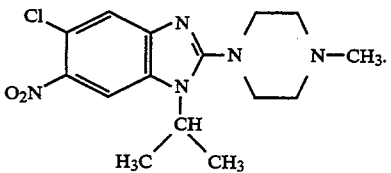

* * * * *